United States Patent
Teverovskiy et al.

(10) Patent No.: US 11,028,252 B2
(45) Date of Patent: Jun. 8, 2021

(54) MELT ADDITIVE COMPOUNDS, METHODS OF USING THE SAME, AND ARTICLES AND COMPOSITIONS INCLUDING THE SAME

(71) Applicant: 3M INNOVATIVE PROPERTIES COMPANY, St. Paul, MN (US)

(72) Inventors: Georgiy Teverovskiy, St. Louis Park, MN (US); Chetan P. Jariwala, Woodbury, MN (US); Ajay K. Vidyasagar, Houston, TX (US); Maria A. Appeaning, St. Paul, MN (US); Kristy A. Jost, Woodbury, MN (US); Robert A. Polik, Minneapolis, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 18 days.

(21) Appl. No.: 16/621,757

(22) PCT Filed: Jun. 5, 2018

(86) PCT No.: PCT/IB2018/054028
§ 371 (c)(1),
(2) Date: Dec. 12, 2019

(87) PCT Pub. No.: WO2018/229596
PCT Pub. Date: Dec. 20, 2018

(65) Prior Publication Data
US 2020/0207948 A1 Jul. 2, 2020

Related U.S. Application Data

(60) Provisional application No. 62/518,930, filed on Jun. 13, 2017.

(51) Int. Cl.
| | | |
|---|---|---|
| C08K 5/435 | (2006.01) | |
| C07D 295/26 | (2006.01) | |
| D01F 1/10 | (2006.01) | |
| D01F 6/62 | (2006.01) | |
| D04H 1/732 | (2012.01) | |
| D04H 3/011 | (2012.01) | |

(52) U.S. Cl.
CPC ............ C08K 5/435 (2013.01); C07D 295/26 (2013.01); D01F 1/10 (2013.01); D01F 6/62 (2013.01); D04H 1/732 (2013.01); D04H 3/011 (2013.01)

(58) Field of Classification Search
CPC ........... C07D 295/26; D01F 1/10; D01F 6/62; D04H 1/732; D04H 3/011
See application file for complete search history.

(56) References Cited

U.S. PATENT DOCUMENTS

| | | | |
|---|---|---|---|
| 5,451,622 A | 9/1995 | Boardman | |
| 5,898,046 A | 4/1999 | Raiford | |
| 5,919,847 A * | 7/1999 | Rousseau | B01D 39/08 524/89 |
| 5,977,390 A | 11/1999 | Raiford | |
| 6,114,419 A | 9/2000 | Liss | |
| 7,396,866 B2 | 7/2008 | Jariwala | |
| 10,662,165 B2 * | 5/2020 | Teverovskiy | C07D 295/26 |
| 10,731,054 B2 * | 8/2020 | Appeaning | C09J 7/201 |
| 10,731,055 B2 * | 8/2020 | Appeaning | C09J 7/203 |
| 2005/0042758 A1 * | 2/2005 | Zyhowski | G01N 31/22 436/3 |

FOREIGN PATENT DOCUMENTS

| | | |
|---|---|---|
| EP | 0592884 | 4/1994 |
| WO | WO 2016-069674 | 5/2016 |
| WO | WO 2017-074709 | 5/2017 |
| WO | WO 2017-074817 | 5/2017 |
| WO | WO 2017-100045 | 6/2017 |
| WO | WO 2017-189684 | 11/2017 |
| WO | WO 2018-005285 | 1/2018 |
| WO | WO 2018-048675 | 3/2018 |
| WO | WO 2018-093623 | 5/2018 |
| WO | WO 2018-169642 | 9/2018 |

OTHER PUBLICATIONS

International Search Report for PCT International Application No. PCT/IB2018/054028, dated Aug. 10, 2018, 4 pages.

\* cited by examiner

*Primary Examiner* — John E Uselding
(74) *Attorney, Agent, or Firm* — Bradford B. Wright

(57) ABSTRACT

A melt additive compound has the general formula (I) wherein R represents a linear alkylene group having from 1 to 18 carbon atoms; n represents an integer from 1 to 4, inclusive; and $R_f^1$ is represented by the general formula II wherein $R_f$ represents a perfluorinated group having from 3 to 5 carbon atoms. Compositions comprising a thermoplastic polymer and the melt additive compound, methods of extruding them and extruded articles are also disclosed.

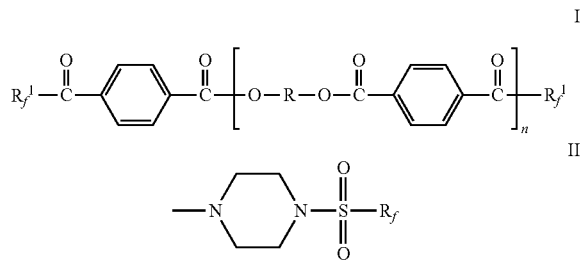

17 Claims, No Drawings

MELT ADDITIVE COMPOUNDS, METHODS OF USING THE SAME, AND ARTICLES AND COMPOSITIONS INCLUDING THE SAME

TECHNICAL FIELD

The present disclosure broadly relates to melt additive compounds suitable for use in polymer extrusion.

BACKGROUND

Certain partially-fluorinated small molecule compounds have been utilized as melt additives to thermoplastics such as polypropylene, and polyester and polyamide blends. Accordingly, extrusion of thermoplastics containing these melt additives may impart static and dynamic water and oil repellency, and soil resistance, to resulting articles such as films and fibers.

For example, partially-fluorinated amides suitable for use as melt-additives has been disclosed in U.S. Pat. No. 5,451,622 (Boardman et al.).

Partially-fluorinated melt additives such as those disclosed in U.S. Pat. No. 5,977,390 (Raiford et al.), U.S. Pat. No. 5,898,046 (Raiford et al.) and U.S. Pat. No. 7,396,866 B2 (Jariwala et al.) are often made using expensive raw materials and may lack durability in polymers other than polypropylene.

Polyesters and polyamides are widely used in films, textiles, and carpet fibers.

SUMMARY

It would be desirable to have new melt additive compounds that are useful for imparting at least one of static and dynamic water and oil repellency, and/or soil resistance, to extruded articles such as films and fibers. This is especially true for polyesters (e.g., polyethylene terephthalate and polycaprolactone) and polyamides (e.g., Nylon 6 and Nylon 6,6 polyamides).

Advantageously, the present disclosure overcomes these problems through the development of new partially-fluorinated compounds that are suitable for use as melt additives in polyesters and polyamides.

In a first aspect, the present disclosure provides a melt additive compound represented by the general formula:

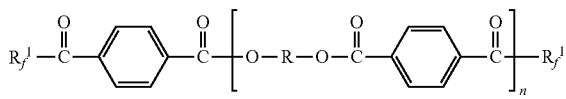

wherein:
R represents a linear alkylene group having from 1 to 18 carbon atoms;
n represents an integer from 1 to 4, inclusive; and
$R_f^1$ is represented by the general formula

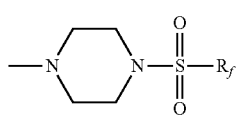

wherein $R_f$ represents a perfluorinated group having from 3 to 5 carbon atoms.

In a second aspect, the present disclosure provides a composition comprising a thermoplastic polymer and a melt additive compound according to the present disclosure.

Compositions according to the present disclosure are generally suitable for use in fibers, and especially fibers that are dyed with dye.

In yet another aspect, the present disclosure provides a method comprising extruding a composition a thermoplastic polymer and a melt additive compound according to the present disclosure.

Features and advantages of the present disclosure will be further understood upon consideration of the detailed description as well as the appended claims.

DETAILED DESCRIPTION

Compounds useful as melt additives according to the present disclosure are represented by general formula I, below:

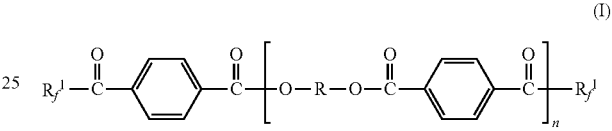

R represents a linear alkylene group having from 1 to 18 carbon atoms, preferably from 2 to 12 carbon atoms, and more preferably from 2 to 8 carbon atoms, and even more preferably 2 to 6 carbon atoms. Exemplary groups R include ethylene, propane-1,3-diyl, butane-1,4-diyl, pentane-1,5-diyl, hexane-1,6-diyl, octane-1,8-diyl, decane-1,10-diyl, dodecane-1,12-diyl, hexadecane-1,16-diyl, and octadecane-1,18-diyl.

n represents an integer from 1 to 4, inclusive (i.e., n=1, 2, 3, or 4).

$R_f^1$ represents a monovalent group represented by the general formula

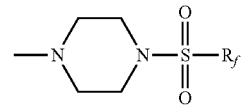

wherein $R_f$ represents a perfluorinated group having from 3 to 5 carbon atoms, preferably $R_f$ has 4 carbon atoms. Examples of groups $R_f$ include perfluoro-n-pentyl, perfluoro-n-butyl, perfluoro-n-propyl, perfluoroisopropyl, and perfluoroisobutyl.

Compounds according to general formula I can be made by any suitable method. One relatively convenient method involves reaction of one acyl chloride group from each of two terephthaloyl chloride molecules with a diol to create an extended diacyl chloride, which is then reacted with two equivalents of a fluorinated piperazine represented by the general formula II, below:

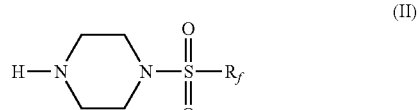

to form the corresponding melt additive compound; for example, as shown in Examples 1 to 4, hereinbelow. Examples of suitable diols include ethylene glycol, 1,3-propanediol, 1,4-butanediol, 1,5-pentanediol, 1,6-hexanediol, 1,8-octanediol, 1,10-decanediol, 1,12-dodecanediol, 1-16-hexadecanediol, and 1,18-octadecanediol. Such diols are available from commercial sources.

Fluorinated piperazines according to general formula II can be prepared using known organic reactions such as, for example, those disclosed in U.S. Pat. No. 5,451,622 (Boardman et al.). An exemplary method of preparation is by the reaction of fluoroaliphatic sulfonyl fluorides, $R_fSO_2F$, with piperazine.

Compounds according to the present disclosure can be combined with extrudable compositions (e.g., one or more thermoplastic polymers) and formed into an extruded article. Examples of extruded articles include sheets, films, fibers and molded articles. Typically the amount of additive to add is an effective amount, preferably from 0.01 to 5 weight percent, more preferably 0.1 to 3 weight percent, and more preferably 0.3 to 1.5 weight percent, based on the total weight of the composition.

Advantageously, melt additive compounds according to the present disclosure may still be receptive to dyes (e.g., textile dyes), while displaying a reasonable degree of water and oil repellency. Accordingly, melt additive compounds according to the present disclosure may be suitable for textile applications including carpet and woven, nonwoven or knit fabrics, for example.

Examples of extrudable polymers include thermoplastic polymers (preferably non-fluorinated) such as polyesters (e.g., polyethylene terephthalate, polybutylene terephthalate, and polycaprolactone), cellulosics (e.g., cellulose acetate and cellulose butyrate), polyamides (e.g., Nylon 6 and Nylon 6,6), polyimides, polyolefins (e.g., polyethylenes, polypropylenes, and polybutylenes), polyetherketone (PEK), polyetheretherketone (PEEK), polycarbonates, and polyacrylics (e.g., polyacrylonitrile and polymethyl methacrylate), and combinations thereof.

Extrudable compositions may contain other ingredients such as for example, fillers, antioxidants, conductive materials, fillers, lubricants, pigments, plasticizers, processing aids, and UV-light stabilizers.

Dyes such as textile dyes are soluble colored organic compounds that are usually applied to textiles from a solution in water. They are designed to bond strongly to the polymer molecules that make up the textile fiber.

The *Colour Index International*, 3$^{rd}$ Ed. 4$^{th}$ Revision, 1992, published by the Society of Dyers and Colourists, Bradford, England is a comprehensive list of known commercial dyes and is updated regularly. Examples include acid dyes, metal-complex dyes, direct dyes, basic dyes, reactive dyes, vat dyes, sulfur dyes. Other dye lists are widely available on the internet.

The compositions may be extruded using screw extruders such as single-screw and twin-screw extruders, for example.

While individual compounds according to the present disclosure may be used as melt additives, mixtures including two or more of these melt additives may also be used.

Select Embodiments of the Present Disclosure

In a first embodiment, the present disclosure provides a melt additive compound represented by the general formula:

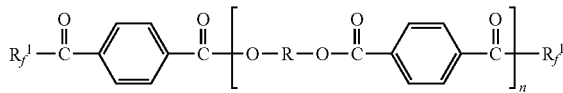

wherein:
R represents a linear alkylene group having from 1 to 18 carbon atoms;
n represents an integer from 1 to 4, inclusive; and
$R_f^1$ is represented by the general formula

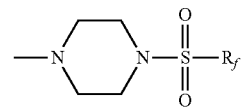

wherein $R_f$ represents a perfluorinated group having from 3 to 5 carbon atoms.

In a second embodiment, the present disclosure provides a melt additive compound according to the first embodiment, wherein R has from 2 to 8 carbon atoms.

In a third embodiment, the present disclosure provides a melt additive compound according to the first embodiment, wherein R has from 2 to 6 carbon atoms.

In a fourth embodiment, the present disclosure provides a melt additive compound according to any one of the first to third embodiments, wherein n is 1 or 2.

In a fifth embodiment, the present disclosure provides a melt additive compound according to any one of the first to fourth embodiments, wherein $R_f$ has 4 carbon atoms.

In a sixth embodiment, the present disclosure provides a composition comprising a thermoplastic polymer and a melt additive compound represented by the general formula:

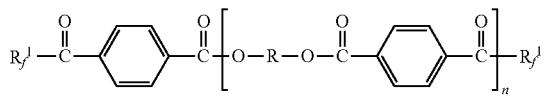

wherein:
R represents a linear alkylene group having from 1 to 18 carbon atoms;
n represents an integer from 1 to 4, inclusive; and
$R_f^1$ is represented by the general formula

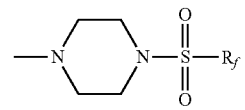

wherein $R_f$ represents a perfluorinated group having from 3 to 5 carbon atoms.

In a seventh embodiment, the present disclosure provides a composition according to the sixth embodiment, wherein R has from 2 to 8 carbon atoms.

In an eighth embodiment, the present disclosure provides a melt additive compound according to the sixth embodiment, wherein R has from 2 to 6 carbon atoms.

In a ninth embodiment, the present disclosure provides a composition according to any one of the sixth to eighth embodiments, wherein n is 1 or 2.

In a tenth embodiment, the present disclosure provides a composition according to any one of the sixth to ninth embodiments, wherein $R_f$ has 4 carbon atoms.

In an eleventh embodiment, the present disclosure provides a fiber comprising a composition according to any one of the sixth to tenth embodiments.

In a twelfth embodiment, the present disclosure provides a fiber according to the eleventh embodiment, wherein the fiber further comprises a dye.

In a thirteenth embodiment, the present disclosure provides a method comprising extruding a composition a thermoplastic polymer and a melt additive compound represented by the general formula:

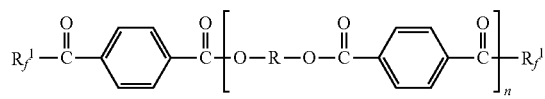

wherein:
R represents a linear alkylene group having from 1 to 18 carbon atoms;
n represents an integer from 1 to 4, inclusive; and
$R_f^1$ is represented by the general formula

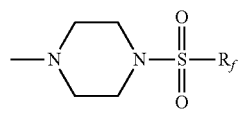

wherein $R_f$ represents a perfluorinated group having from 3 to 5 carbon atoms.

In a fourteenth embodiment, the present disclosure provides a method according to the thirteenth embodiment, wherein R has from 2 to 8 carbon atoms.

In a fifteenth embodiment, the present disclosure provides a method according to the thirteenth embodiment, wherein R has from 2 to 6 carbon atoms.

In a sixteenth embodiment, the present disclosure provides a method according to any one of the thirteenth to fifteenth embodiments, wherein n is 1 or 2.

In a seventeenth embodiment, the present disclosure provides a method according to any one of the thirteenth to sixteenth embodiments, wherein $R_f$ has 4 carbon atoms.

Objects and advantages of this disclosure are further illustrated by the following non-limiting examples, but the particular materials and amounts thereof recited in these examples, as well as other conditions and details, should not be construed to unduly limit this disclosure.

EXAMPLES

Unless otherwise noted, all parts, percentages, ratios, etc. in the Examples and the rest of the specification are by weight. Unless otherwise indicated, materials used in the examples available from commercial suppliers (e.g., Aldrich Chemical Co., Milwaukee, Wis.) and/or can be made by known methods. Materials prepared in the examples were analyzed by NMR spectroscopy and were consistent with the given structures.

| TABLE OF MATERIALS USED IN THE EXAMPLES | |
|---|---|
| DESIGNATION | DESCRIPTION |
| Piperazine | Piperazine, available as product code A15049 from Alfa Aesar Co., Tewksbury, Massachusetts |
| Perfluorobutanesulfonyl fluoride | Perfluorobutanesulfonyl fluoride, available from Sigma-Aldrich Co., St. Louis, Missouri. |
| Terephthaloyl Chloride | Terephthaloyl Chloride, available as product code 120871 from Sigma-Aldrich, St. Louis, Missouri |
| Ethylene Glycol | Ethylene Glycol, available as product code 324558 from Sigma-Aldrich, St. Louis, Missouri |
| 1,4-butanediol | 1,4-butanediol, available as product code 493732 from Sigma-Aldrich, St. Louis, Missouri |
| 1,6-hexanediol | 1,6-hexanediol, available as product code 240117 from Sigma-Aldrich, St. Louis, Missouri |
| Kaydol mineral oil | KAYDOL white mineral oil from Sonneborn Refined Products, Parsippany, New Jersey |
| Bis(2-hydroxyethyl) terephthalate | Bis(2-hydroxyethyl) terephthalate, available as product code 465151 from Sigma-Aldrich |
| Disperse Blue Dye | Amecron Blue AC-E dye |
| PBSP | Monovalent group 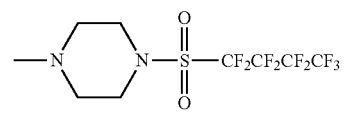 |
| Comparative Additive A | Comparative Additive A was fluorochemical diester F-8 prepared in U.S. Pat. No. 7,396,866 B2 (Jariwala et al.), and has the formula: $C_4F_9SO_2N(CH_3)CH_2CH_2OC(=O)(CH_2)_{16}C(=O)OCH_2CH_2N(CH_3)SO_2C_4F_9$ |

-continued

TABLE OF MATERIALS USED IN THE EXAMPLES

| DESIGNATION | DESCRIPTION |
|---|---|
| PET Pellets | Nan Ya 0.375 IV PET resin available from Nan Ya Plastics Co., Wharton, Texas |

"PBSP" refers to the monovalent group

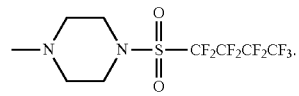

Water Repellency Test

Nonwoven web samples were evaluated for water repellency by challenging test samples to penetrations by blends of deionized water and isopropyl alcohol (IPA). Each blend is assigned a rating number as shown below:

| Water Repellency Rating Number | Blend (% by volume) |
|---|---|
| 0 | 100% water |
| 1 | 90/10 water/IPA |
| 2 | 80/20 water/IPA |
| 3 | 70/30 water/IPA |
| 4 | 60/40 water/IPA |
| 5 | 50/50 water/IPA |
| 6 | 40/60 water/IPA |
| 7 | 30/70 water/IPA |
| 8 | 20/80 water/IPA |
| 9 | 10/90 water/IPA |
| 10 | 100% IPA |

In running the Water Repellency Test, a nonwoven web sample is placed on a flat, horizontal surface. Five small drops of water or a water/IPA mixture are gently placed at points at least two inches (5.1 cm) apart on the sample. If, after observing for ten seconds at a 45° angle, four of the five drops are visible as a sphere or a hemisphere, the nonwoven web sample is deemed to pass the test. The reported water repellency rating corresponds to the highest numbered water or water/IPA mixture for which the nonwoven sample passes the described test. It is desirable to have a water repellency rating of at least 4, preferably at least 6.

Oil Repellency Test

Nonwoven web samples were evaluated for oil repellency by challenging test samples to penetration by oil or oil mixtures of varying surface tensions. Oils and oil mixtures are given a rating corresponding to the following:

| Oil Repellency Rating Number | Oil Composition |
|---|---|
| 0 | fails Kaydol mineral oil |
| 1 | Kaydol mineral oil |
| 2 | 65/35 (by volume) mineral oil/n-hexadecane |
| 3 | n-hexadecane |
| 4 | n-tetradecane |
| 5 | n-dodecane |
| 6 | n-decane |
| 7 | n-octane |
| 8 | n-heptane |

The Oil Repellency Test is run in the same manner as is the Water Repellency Test (hereinabove), with the reported oil repellency rating corresponding to the highest oil or oil mixture for which the nonwoven web sample passes the test. It is desirable to have an oil repellency rating of at least 1, preferably at least 3.

Melt Blown Extrusion Procedure

The extruder used was a Brabender CTSE-V counter-rotating conical twin screw extruder (Brabender GmbH & Co KG, Duisberg, Germany) with a maximum extrusion temperature of approximately 275° C., and with the distance to the collector of approximately 2.75 inches (7.0 cm).

The fluorochemical and thermoplastic polymer were each weighed. The fluorochemical and thermoplastic polymer were then added simultaneously to the extruder at varying rates to maintain 9.85 lbs/hr (4.47 kg/1117) of polymer and 0.15 lbs/hr (0.068 kg/hr) of fluorochemical additive to maintain a total throughput rate of 10 lbs/hr (4.5 kg/hr).

The process conditions for each mixture were the same, including the melt blowing die construction used to blow the microfiber web, the basis weight of the web ($100\pm5$ g/m$^2$) and the diameter of the microfibers (10 to 20 micrometers). The extrusion temperature was approximately 265° C., the primary air temperature was 265° C., the pressure was 5 psi (34 kPa), with a 0.030 inch (0.76 cm) air gap width and the polymer throughput rate was about 10 lbs/hr (4.5 kg/hr).

Dyeing Procedure

Dyeing is performed using an Ahiba Dyde machine under the following conditions: Amecron Blue AC-E (Disperse Blue) dye; 100:1 liquor ratio; 2% Depth of Shade; 1 g/L Glucopan; 2 g/L Benzyl Alcohol. The dyeing program heats as quickly as possible to 90° C., remains there for 30 minutes, and then cools back down to room temperature as quickly as possible.

Preparation of 1-(1,1,2,2,3,3,4,4,4-Nonafluorobutylsulfonyl)Piperazine

To a 3-neck 3 L round bottom equipped with a mechanical stirrer, addition funnel and a Claisen adaptor with thermocouple and reflux condenser was added piperazine (486 g, 5642 mmol) and triethylamine (400 mL, 2870 mmol). The reaction mixture was heated to 65° C. with continuous stirring. Once the reaction mixture reached 50° C., 1,1,2,2,3,3,4,4,4-nonafluorobutane-1-sulfonyl fluoride (500 mL, 2780 mmol) was added via addition funnel at such a rate so as to maintain a temperature below 90° C. Upon completion of addition, the temperature was raised to 95° C. and the reaction mixture was allowed to stir for 16 hr. The vessel was cooled to 50° C. and water (300 mL) was added followed by dichloromethane (500 mL). The resulting biphasic mixture was allow to stir for 5 min and then allowed to phase separate. The lower phase was removed, washed 3× with water (300 mL), brine (500 mL), and dried over sodium sulfate (250 g). The resulting yellow solution was filtered, solvent was removed via rotary evaporator and distilled at 250 mTorr (33.3 mPa) and 80° C. to afford 713 g of 1-(1,1,2,2,3,3,4,4,4-nonafluorobutylsulfonyl)piperazine as a white solid.

Example 1

Solution A (a mixture of 68.7 g (1.99 equivalents) of terephthaloyl chloride and 100 mL of ethyl acetate) was added to a 3-L round bottom flask equipped with a mechanical stirrer, reflux condenser, and an addition funnel containing Solution B (a mixture of 8 mL, 1 equivalent of ethylene glycol, 2 equivalents of N-ethyldiisopropylamine, and 100 mL of ethyl acetate). Solution B was then added dropwise to Solution A with vigorous stirring. The mixture was allowed to stir for 1 hr. Solution C (a mixture of 2.01 equivalents of 1-(1,1,2,2,3,3,4,4,4-nonafluorobutylsulfonyl)piperazine, 2 equivalents of N-ethyldiisopropylamine, and 100 mL of ethyl acetate) was then added dropwise to the reaction mixture with vigorous stirring. An exotherm was observed. The mixture was allowed to stir for 16 h after which 500 mL of water was added. The resulting biphasic mixture was filtered, washed with water (3×500 mL), 1 M HCl (100 mL), and water again (3×500 mL) to afford ethane-1,2-diyl bis (4-(4-((perfluorobutyl)sulfonyl)piperazine-1-carbonyl)benzoate) as a white solid, structure shown below:

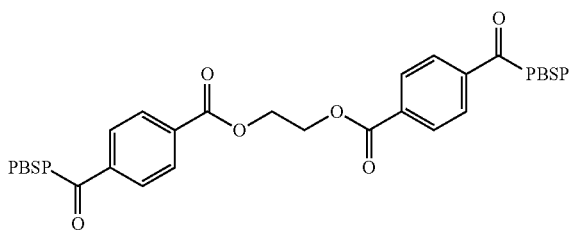

Example 2

Solution A (a mixture of 68.7 g (1.99 equivalents) of terephthaloyl chloride and 100 mL of ethyl acetate) was added to a 3-L round bottom flask equipped with a mechanical stirrer, reflux condenser, and an addition funnel containing Solution B (a mixture of 15 mL, 1 equivalent of 1,4-butanediol, 59.3 mL (2 equivalents) of N-ethyldiisopropylamine, and 100 mL of ethyl acetate). Solution B was then added dropwise to Solution A with vigorous stirring. The mixture was allowed to stir for 1 hr. Solution C (a mixture of 2.01 equivalents of 1-(1,1,2,2,3,3,4,4,4-nonafluorobutylsulfonyl)piperazine, 59.3 mL (2 equivalents) of N-ethyldiisopropylamine, and 100 mL of ethyl acetate) was then added dropwise to the reaction mixture with vigorous stirring. An exotherm was observed. The mixture was allowed to stir for 16 h after which 1 mole of water was added. The resulting biphasic mixture was filtered, washed with water (3×500 mL), 1 M HCl (100 mL), and water again (3×500 mL) to afford butane-1,4-diyl bis(4-(4-((perfluorobutyl)sulfonyl)piperazine-1-carbonyl)benzoate) as a white solid, structure shown below:

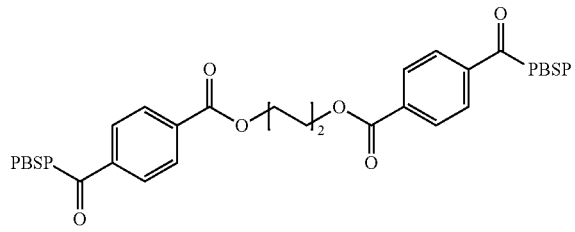

Example 3

Solution A (a mixture of 68.7 g (1.99 equivalents) of terephthaloyl chloride and 100 mL of ethyl acetate) was added to a 3-L round bottom flask equipped with a mechanical stirrer, reflux condenser, and an addition funnel containing Solution B (a mixture of 20 g (1 equivalent) of 1,6-hexanediol, 59.3 mL (2 equivalents) of N-ethyldiisopropylamine, and 100 mL of ethyl acetate). Solution B was then added dropwise to Solution A with vigorous stirring. The mixture was allowed to stir for 1 hr. Solution C (a mixture of 2.01 equivalents of 1-(1,1,2,2,3,3,4,4,4-nonafluorobutylsulfonyl)piperazine, 59.3 mL (2 equivalents) of N-ethyldiisopropylamine, and 100 mL of ethyl acetate) was then added dropwise to the reaction mixture with vigorous stirring. An exotherm was observed. The mixture was allowed to stir for 16 h after which 1 mole of water was added. The resulting biphasic mixture was filtered, washed with water (3×500 mL), 1 M HCl (100 mL), and water again (3×500 mL) to afford hexane-1,4-diyl bis(4-(4-((perfluorobutyl)sulfonyl)piperazine-1-carbonyl)benzoate) as a white solid, structure shown below:

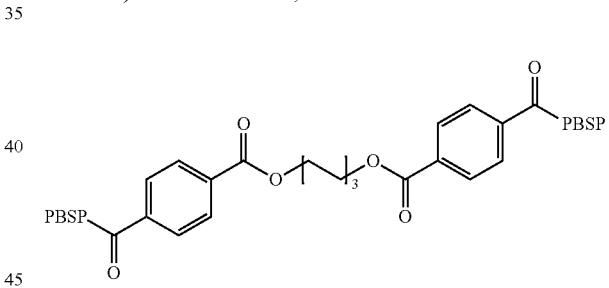

Example 4

Solution A (a mixture of 68.7 g (1.99 equivalents) of terephthaloyl chloride and 100 mL of ethyl acetate) was added to a 3-L round bottom flask equipped with a mechanical stirrer, reflux condenser, and an addition funnel containing Solution B (a mixture of 40 g (1 equivalent) of di(2-hydroxyethyl) terephthalate), 59.3 mL (2 equivalents) of N-ethyldiisopropylamine, and 100 mL of ethyl acetate). Solution B was then added dropwise to Solution A with vigorous stirring. The mixture was allowed to stir for 1 hr. Solution C (a mixture of 2.01 equivalents of 1-(1,1,2,2,3,3,4,4,4-nonafluorobutylsulfonyl)piperazine, 59.3 mL (2 equivalents) of N-ethyldiisopropylamine, and 100 mL of ethyl acetate) was then added dropwise to the reaction mixture with vigorous stirring. An exotherm was observed. The mixture was allowed to stir for 16 h after which 1 mole of water was added. The resulting biphasic mixture was filtered, washed with water (3×500 mL), 1 M HCl (100 mL), and water again (3×500 mL) to afford bis(2-((4-(4-((perfluorobutyl)sulfonyl)piperazine-1-carbonyl)benzoyl)oxy)ethyl) terephthalate as a white solid mixture containing of 65% of n=1 oligomer having the structure shown below

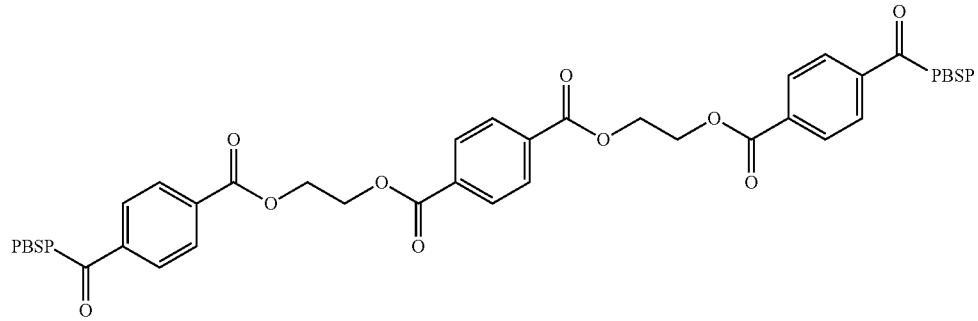

and 35% of material having the structure shown below

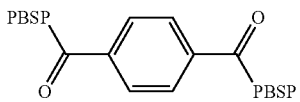

Examples 5-8 and Comparative Examples A-B

PET pellets were independently co-extruded with 1.5 wt. percent of the melt additives of Examples 1-4 and Comparative Example A to form meltblown nonwovens. The nonwoven fabrics were annealed at 160° C. for 2 min. Replicates of the meltblown fabrics were dyed with disperse blue dye according to the Dyeing Procedure, and then annealed at 160° C. for 2 min. The resulting fabrics were evaluated utilizing a water repellency test by varying the weight percent of isopropanol (IPA) in water, and determining the highest weight percent IPA solution that was able to maintain discrete droplets on the coated surface for at least 30 seconds prior to wetting out the fabric. They were further evaluated for oil and water repellency utilizing the Water and Oil Repellency Tests. Results are reported in Table 1 (below).

What is claimed is:

1. A melt additive compound represented by the general formula:

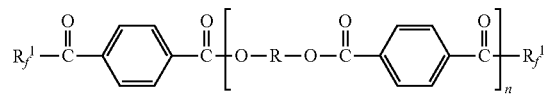

wherein:
R represents a linear alkylene group having from 1 to 18 carbon atoms;
n represents an integer from 1 to 4, inclusive; and
$R_f^1$ is represented by the general formula

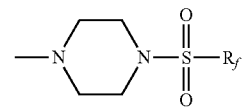

wherein $R_f$ represents a perfluorinated group having from 3 to 5 carbon atoms.

2. The compound of claim 1, wherein R has from 2 to 8 carbon atoms.

TABLE 1

| EXAMPLE | ADDITIVE | OIL REPELLENCY, UNDYED | MAXIMUM WEIGHT PERCENT IPA IN WATER, UNDYED | OIL REPELLENCY, DYED | MAXIMUM WEIGHT PERCENT IPA IN WATER, DYED |
|---|---|---|---|---|---|
| 5 | EXAMPLE 1 | 8 | 100 | 5 | 30 |
| 6 | EXAMPLE 2 | 8 | 100 | 8 | 100 |
| 7 | EXAMPLE 3 | 8 | 100 | 1 | 10 |
| 8 | EXAMPLE 4 | 8 | 100 | 6 | 70 |
| COMPARATIVE EXAMPLE A | COMPARATIVE ADDITIVE A | 4 | 60 | 0 | 20 |
| COMPARATIVE EXAMPLE B | NONE | 0 | 10 | 0 | 10 |

All cited references, patents, and patent applications in the above application for letters patent are herein incorporated by reference in their entirety in a consistent manner. In the event of inconsistencies or contradictions between portions of the incorporated references and this application, the information in the preceding description shall control. The preceding description, given in order to enable one of ordinary skill in the art to practice the claimed disclosure, is not to be construed as limiting the scope of the disclosure, which is defined by the claims and all equivalents thereto.

3. The compound of claim 1, wherein R has from 2 to 6 carbon atoms.

4. The compound of claim 1, wherein n is 1 or 2.

5. The compound of claim 1, wherein $R_f$ has 4 carbon atoms.

6. A composition comprising a thermoplastic polymer and a melt additive compound represented by the general formula:

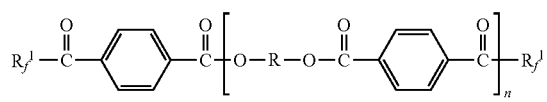

wherein:
R represents a linear alkylene group having from 1 to 18 carbon atoms;
n represents an integer from 1 to 4, inclusive; and
$R_f^1$ is represented by the general formula

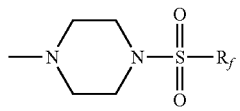

wherein $R_f$ represents a perfluorinated group having from 3 to 5 carbon atoms.

7. The composition of claim 6, wherein R has from 2 to 8 carbon atoms.

8. The composition of claim 6, wherein R has from 2 to 6 carbon atoms.

9. The composition of claim 6, wherein n is 1 or 2.

10. The composition of claim 6, wherein $R_f$ has 4 carbon atoms.

11. A fiber comprising the composition of claim 6.

12. The fiber of claim 11, wherein the fiber further comprises a dye.

13. A method comprising extruding a composition a thermoplastic polymer and a melt additive compound represented by the general formula:

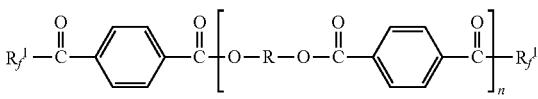

wherein:
R represents a linear alkylene group having from 1 to 18 carbon atoms;
n represents an integer from 1 to 4, inclusive; and
$R_f^1$ is represented by the general formula

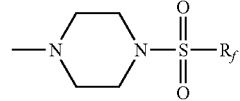

wherein $R_f$ represents a perfluorinated group having from 3 to 5 carbon atoms.

14. The method of claim 13, wherein R has from 2 to 8 carbon atoms.

15. The method of claim 13, wherein R has from 2 to 6 carbon atoms.

16. The method of claim 13, wherein n is 1 or 2.

17. The method of claim 13, wherein $R_f$ has 4 carbon atoms.

* * * * *